(12) United States Patent
Gu et al.

(10) Patent No.: US 12,576,111 B2
(45) Date of Patent: Mar. 17, 2026

(54) APPLICATION OF BMSC-EXOS IN TREATING PD

(71) Applicant: NANTONG UNIVERSITY, Jiangsu (CN)

(72) Inventors: Xiaosong Gu, Jiangsu (CN); Cheng Sun, Jiangsu (CN); Fei Ding, Jiangsu (CN); Leilei Gong, Jiangsu (CN); Meng Cong, Jiangsu (CN); Xiaomin Wang, Jiangsu (CN); Hualin Sun, Jiangsu (CN); Yu Zhang, Jiangsu (CN); Lili Zhao, Jiangsu (CN); Tianmei Qian, Jiangsu (CN)

(73) Assignee: NANTONG UNIVERSITY (CN)

( * ) Notice: Subject to any disclaimer, the term of this patent is extended or adjusted under 35 U.S.C. 154(b) by 0 days.

(21) Appl. No.: 18/548,181

(22) PCT Filed: Oct. 19, 2022

(86) PCT No.: PCT/CN2022/126041
§ 371 (c)(1),
(2) Date: Aug. 28, 2023

(87) PCT Pub. No.: WO2023/179001
PCT Pub. Date: Sep. 28, 2023

(65) Prior Publication Data
US 2025/0127817 A1 Apr. 24, 2025

(30) Foreign Application Priority Data
May 31, 2022 (CN) .......................... 202210607894.5

(51) Int. Cl.
*A61K 35/28* (2015.01)
*A61K 9/50* (2006.01)
(Continued)

(52) U.S. Cl.
CPC ............ *A61K 35/28* (2013.01); *A61K 9/5068* (2013.01); *A61P 25/16* (2018.01); *C12N 5/0663* (2013.01)

(58) Field of Classification Search
CPC ....... A61K 35/28; A61K 9/5068; A61P 25/16; C12N 5/0663
See application file for complete search history.

(56) References Cited

U.S. PATENT DOCUMENTS

2010/0136687 A1* 6/2010 Westover ................ A61P 13/00
435/395
2020/0400687 A1* 12/2020 Chase ................ G01N 33/6896

FOREIGN PATENT DOCUMENTS

CN 111471647 A * 7/2020 ........... C12N 5/0663
CN 107043745 B * 8/2020 ........... C12N 5/0663
(Continued)

*Primary Examiner* — Jianfeng Song

(57) ABSTRACT

An application of Bone Marrow Mesenchyml Stem Cell Exosomes (BMSC-Exos) in treating Parkinson's disease (PD) is provided, wherein the BMSC-Exos are generated by stimulating BMSCs with a culture solution and extracted from the culture solution after passage; and the culture solution of the BMSCs is an α-MEM culture solution containing FBS and PS. The BMSC-Exos can greatly improve a motor function of a model mouse with PD, protect dopaminergic neurons of the model mouse with PD, improve an olfactory function of the model mouse with PD, and also inhibit the activation of olfactory astrocytes of the model mouse with PD.

7 Claims, 7 Drawing Sheets

(51) Int. Cl.
    *A61P 25/16*     (2006.01)
    *C12N 5/0775*     (2010.01)

(56)           References Cited

FOREIGN PATENT DOCUMENTS

| CN | 111826340 A | * | 10/2020 | ............. | A61K 8/985 |
| CN | 112022882 A | * | 12/2020 | ........... | A61K 31/216 |

* cited by examiner

Control group

MPTP group

MPTP+ exosome group

APPLICATION OF BMSC-EXOS IN TREATING PD

FIELD

The invention belongs to the field of biomedicine, and relates to an application of Bone Marrow Mesenchyml Stem Cell Exosomes (BMSC-Exos) in treating Parkinson's disease (PD).

BACKGROUND

PD, also known as paralysis agitans, is a common senile degenerative neurological disease, with an average age of onset of about 60 years old. Statistics show that one of every 800 people in the world suffers from PD, and the prevalence rate of PD will double by 2030 due to the acceleration of the aging process, expected to exceed 9 million patients. The prevalence rate of people over 65 in China is about 1.7%. The direct medical expenses of patients are expected to exceed $10,000 per year, which brings a heavy burden to families and society. PD is progressive, multiple and occult in onset, mainly manifested as slow movement, myotonia, static tremor and Postural Instability and Gait Disorder (PIGD). In addition. PD also includes a variety of non-motor symptoms, such as depression, constipation, olfactory dysfunction and sleep disorders. The main pathological features of PD include degeneration and death of dopaminergic neurons in substantia nigra, significant decrease in the content of striatal dopamine and appearance of Lewy bodies in substantia nigra. PD is clinically treated with dopamine replacement therapy primarily. Long-term use of the therapy may cause a variety of adverse reactions, such as anxiety, insomnia, hallucination and other psychiatric symptoms. Moreover, the current treatment means can only improve the symptoms of the disease, but cannot stop the progress of the disease, let alone cure the disease. Therefore, it is of great economic and social benefits to find new medicines for treating PD.

SUMMARY

An objective of the invention is to provide an application of BMSC-Exos in treating PD. The BMSC-Exos can greatly improve a motor function of a model mouse with PD, protect dopaminergic neurons of the model mouse with PD, improve an olfactory function of the model mouse with PD, and also inhibit the activation of olfactory astrocytes of the model mouse with PD.

The invention provides the following technical solution:

An application of BMSC-Exos in preparing medicines for treating PD, wherein the BMSC-Exos are generated by stimulating BMSCs with a culture solution and extracted from the culture solution after passage; and the culture solution of the BMSCs is an α-MEM culture solution containing FBS and PS.

Further, the application includes any one of the following:

an application in preparing medicines for improving a motor function in PD;

an application in preparing medicines for protecting dopaminergic neurons in PD;

an application in preparing medicines for improving an olfactory function in PD; and an application in preparing medicines for reducing the activation of astrocytes in olfactory bulbs in PD.

Further, the culture solution is an α-MEM culture solution containing 10% of FBS and 1% of PS.

Further, the BMSCs are cultured at 37° C. and 5% of $CO_2$.

Further, a bone marrow is inoculated in a complete medium preheated at 37° C.

Further, the BMSCs are digested with trypsin when the cell density reaches 80% during culture, and are added with the complete medium to terminate the digestion when it is observed that the cells become round and intercellular spaces become larger under a microscope; supernatant is discarded after centrifugation, and the passage ratio is determined based on the number of cells; the cells are firstly passaged to form a P1 generation; the medium is completely replaced every 2 days, the cells are passaged to form a P2 generation after 4-6 days and then are digested again and passaged to form a P3 generation; and then, the P3 generation is used for extracting BMSC-Exos.

Further, a method for extracting the BMSC-Exos includes the following steps: collecting supernatant of the BMSCs, adding XBB with the same volume as the supernatant of the BMSCs to be mixed uniformly, and filtering and collecting BMSC-Exos with a membrane affinity spin column.

Further, a method for collecting the supernatant of BMSCs includes the following steps: discarding the original culture medium when the P3 generation of BMSCs grows to have a density of 80%; replacing with a serum-free α-MEM culture medium after washing twice with PBS; collecting the culture medium after continuing to culture for 48 h; and filtering to obtain supernatant after removing cell debris through centrifugation.

Further, the filtration method includes filtration with a 0.22 μm filter membrane.

Further, the centrifugation method includes: centrifuging 300 g of culture medium at 4° C. and then centrifuging 2000 g of culture medium for 10 min.

Beneficial Effects

The invention provides an application of BMSC-Exos in treating PD. The BMSC-Exos can greatly improve a motor function of a model mouse with PD, protect dopaminergic neurons of the model mouse with PD, improve an olfactory function of the model mouse with PD, and also inhibit the activation of olfactory astrocytes of the model mouse with PD.

DETAILED DESCRIPTION

Figure 1:
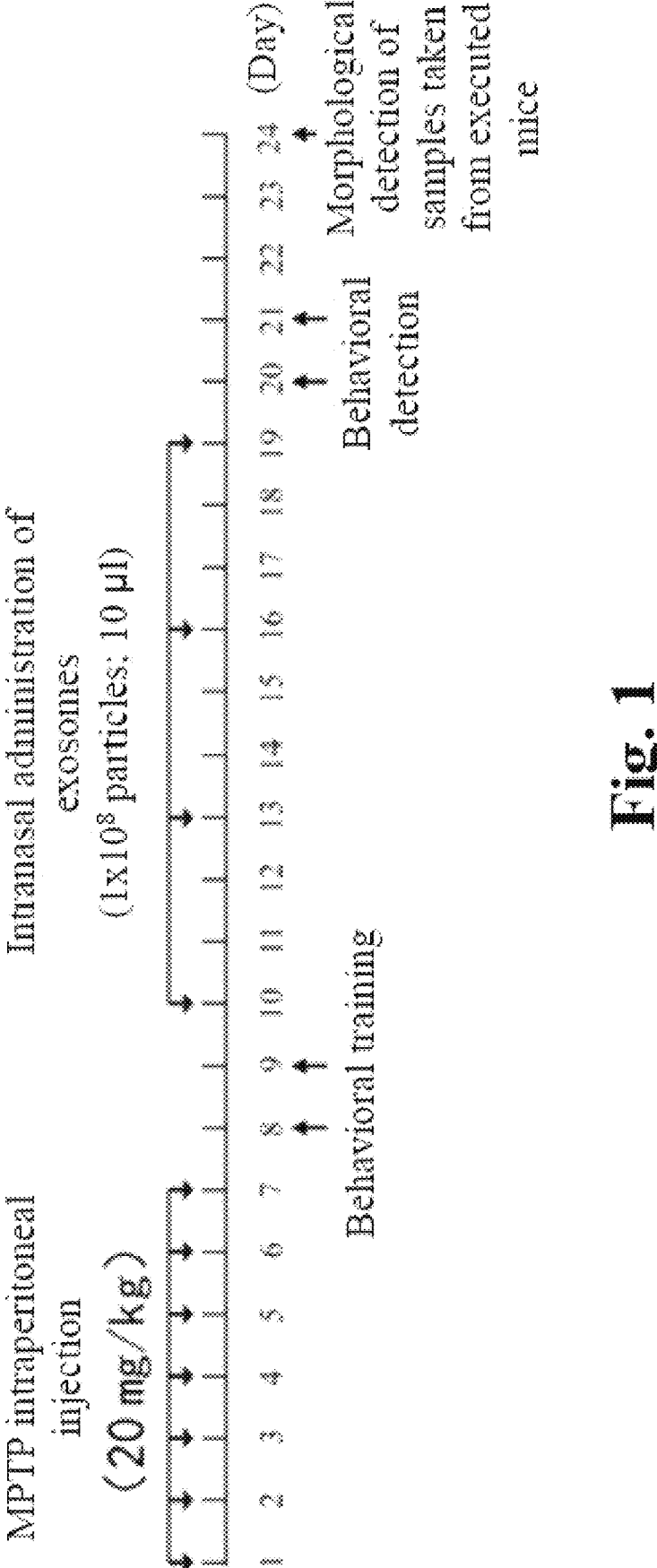
FIG. 1 shows an experimental flow.

As shown in FIG. 1, mice were intraperitoneally injected with MPTP (1-methyl-4-phenyl-1,2,3,6-tetrahydropyridine) at a dose of 20 mg/kg/day for 7 days, and then were used for modeling a model mouse with PD. After modeling, behavioral training was conducted for 2 days, including pole climbing and olfactory functional behavior. The mice were treated by giving exosomes through nasal drip, giving 10 µl of exosomes (including $1 \times 10^8$ exosomes particles) to each mouse every time. The mice were treated once every 2 days, 4 times in total. Behavioral detection and morphological detection were conducted after the treatment (FIG. 1).

Specific steps are as follows:
1. Culture of Human BMSCs (1) Inoculation: 1 ml of bone marrow was inoculated in a 10 cm culture dish (α-MEM culture solution containing 10% of FBS and 1% of PS) containing 8 ml of complete medium preheated at 37° C., mixed uniformly, and incubated in a cell incubator at 37° C. and 5% $CO_2$. The bone marrow was derived from bone marrow of healthy people. The complete medium is an α-MEM medium, containing 10% of fetal bovine serum and 1% of penicillin and streptomycin.

(2) Solution exchange: the solution was half exchanged on the fourth day after inoculation, and was fully exchanged on the seventh day.

(3) Passage: the cells were digested with 1 ml of 0.25% trypsin when the cell density reached 80% or above during culture, and were added with the complete medium to terminate the digestion when it was observed that the cells became round and spaces became larger under a microscope; supernatant was discarded after centrifugation for 5 min at 1000 rpm, and the passage ratio was determined as a P1 generation based on the number of cells; the solution was fully exchanged every 2 days, the cells were passaged to form a P2 generation after 4-6 days and then were digested again and passaged to form a P3 generation; and then, the P3 generation was used for follow-up experiments.
2. Extraction of Exosomes (1) Collection of supernatant of BMSCs: an original culture medium was discarded when the P3 generation human BMSCs grew to have a density of 80%, washed twice with PBS, and then replaced with a serum-free α-MEM culture medium; and the culture medium was collected after continuing to culture for 48 h. 300 g of culture medium was centrifuged at 4° C.; then, 2000 g of culture medium was centrifuged for 10 min; and the culture medium was filtered with a 0.22 µm filter membrane after cell debris was removed, and then stored in a refrigerator at −80° C. for later use.

(2) Extraction of BMSC-Exos: the extraction method, referring to a product manual of exoEasy kit (QIAGEN), includes the following steps:

1) XBB with the same volume as the supernatant of the BMSCs was added to be mixed uniformly.

2) The mixture was added to an exoEasy column: 500 g of the mixture was centrifuged at room temperature for 1 min; liquid in a collecting tube was discarded; and the step was repeated until the mixture was fully filtered.

3) 10 ml of XWB was added: 5000 g of liquid was centrifuged for 5 min; and the collecting tube was discarded.

4) The exoEasy column was placed in a new collecting tube: 1 ml of BPE was added to the surface of the membrane: 500 g of liquid was centrifuged for 5 min: the liquid was transferred to the surface of the membrane again; 5000 g of liquid was centrifuged for 5 min; and samples containing exosomes in a centrifuge tube were collected for the follow-up experiments.
3. Analysis of Exosomes by NTA The extracted exosomes were diluted 1000 times; and the concentration and diameter distribution of exosomes were identified by a Nanoparticle Tracking Analysis (NTA).
4. Observation of Morphology of Exosomes by TEM 1) 20 µl of exosome stock solution was absorbed and dropped on red wax.

2) A copper mesh coated with polyvinyl acetate/carbon in advance was clamped and placed in droplets, and then placed at room temperature for 20 min.

3) 2% paraformaldehyde was immobilized at room temperature for 2 min.

4) 2% phosphotungstic acid (PTA) was used for counter-staining at room temperature for 1 min.

5) An infrared lamp was used for drying.

6) The exosomes were observed and photographed on a machine.
5. Culture of Olfactory Bulb Neurons Adult C57BL/6J mice were killed by breaking necks and then disinfected with ethanol; the heads were dissected from the center and immediately put into PBS containing 1% of PS to clean the blood; olfactory bulbs were taken out through aseptic dissection under a microscope; meninges were peeled off, put into 0.25% of trypsin preheated, cut into small pieces of 0.5 mm³, and acted at 37° C. for 30 min; and then, a DMEM/F12 culture solution containing 10% of fetal bovine serum was used for terminating the digestion of trypsin, and gently blew several times. The prepared cell suspension was centrifuged at 1200 rpm for 5 min; and the supernatant was discarded. A Neurobasal medium containing 1% of glutamine and 2% of B27 was added, sieved with a 400-mesh sieve, and inoculated on a round coverslip coated with L-polylysine. The culture medium was put and cultured in an incubator at 37° C. and 5% carbon dioxide, and exchanged every 2 days. After the neurons grew for 6-7 days, follow-up experiments were conducted.
6. Internalization of Exosomes by Olfactory Bulb Neurons The exosomes were labeled with PKH26, specifically as follows:

(1) A solution (100 µl) containing $1 \times 10^{10}$ exosomes particles was prepared.

(2) The exosomes were added into 500 µl of Diluent C to be mixed gently.

(3) A new EP tube was taken; and 4 µl of PKH26 was added into 500 µl of Diluent C.

(4) (2) was added into (3) to be mixed uniformly.

(5) The solution was placed at room temperature for 4 min, and blew 10 times every 1 min.

(6) Exosomes-free FBS with equal volume was added to stop staining.

(7) An ultrafiltration tube was used for concentration for later use.

(8) The exosomes were added into the olfactory bulb neurons, co-cultured for 12 h, and then stained with an Anti-TUJ1 antibody (1:1000) for immunofluorescence staining; and the exosomes were observed and photographed under a fluorescence microscope.

7. Preparation of Model Mouse with PD and Treatment of Exosomes 12-week-old male C57BL/6J mice were randomly classified into a control group and a model group. The model mice with PD were induced by intraperitoneal injection of neurotoxin MPTP (N-methyl-4-phenyl-1, 2, 3, 6-tetrahydro-pyradine). The dosage of MPTP was 20 mg/kg/day; and the mode of administration was intraperitoneal injection for 7 days. The exosomes were treated by nasal administration, with a dosage of $1\times10^8$ exosome particles and a volume of 10 μl, once every 2 days, 4 times in total.

8. Pole Test

The animal was placed at an apex of a vertically fixed pole (15 mm in diameter and 50 cm in length) with a rough surface; and the time taken by the mouse from the apex to the bottom of the pole was calculated. The detection was conducted at an interval of 5 min, for 5 times in total; and the sum was averaged after removing minimum and maximum values.

9. Olfactory Experiment

A mouse was fasted for 20 h in advance: a clean cage (42 cm in length, 24 cm in width, 15 cm in height) was prepared; and cheese was sequentially buried in the middle, upper left, lower right, upper right and lower left of a clean padding, wherein the cheese should be buried 0.5 cm below the padding. The mouse was put in the cage; and the time for the mouse to find the cheese was calculated. If the cheese was not found within 300 s, it will be recorded as 300 s. Statistical analysis was conducted after removing the minimum and maximum values.

10. Immunofluorescence of Tissues (1) Brain tissues of mice was put in 4% paraformaldehyde and stored in a refrigerator at 4° C.' for 24 h.

(2) 20% and 30% sucrose were prepared with 2) 1×PB and then sequentially dehydrated for 24 h.

(3) The dehydrated brain tissues were frozen and sliced to have a thickness of 12 μm, put in an oven at 37° C. overnight and then stored at −20° C.

(4) The slices were baked at 60° C. for 30 min before staining.

(5) The slices were washed with PBS for 3 times. 5 min for each time.

(6) The slices were sealed with sealing liquid for sealing at 37° C. for 1 h.

(7) The slices were washed with PBS for 3 times, 10 min for each time, and incubated with a TH/GFAP/NeuN antibody at a proper ratio at 4° C. overnight.

(8) The slices were washed with PBS for 3 times, and incubated with a homologous secondary antibody for 1 h at room temperature.

(9) The slices were sealed with fluorescent sealing liquid after being washed with PBS for 3 times, and then observed and photographed with the microscope.

Figure 2:
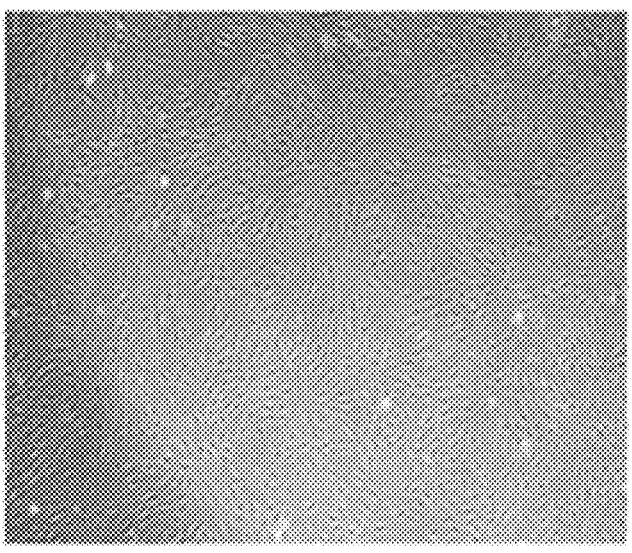
FIG. 2 shows identification of BMSC-Exos; A shows BMSCs; B shows analysis of the prepared exosomes by a Nanoparticle Tracking Analysis (NTA); and C shows observation of the prepared exosomes by a transmission electron microscope (TEM).
Figure 2:
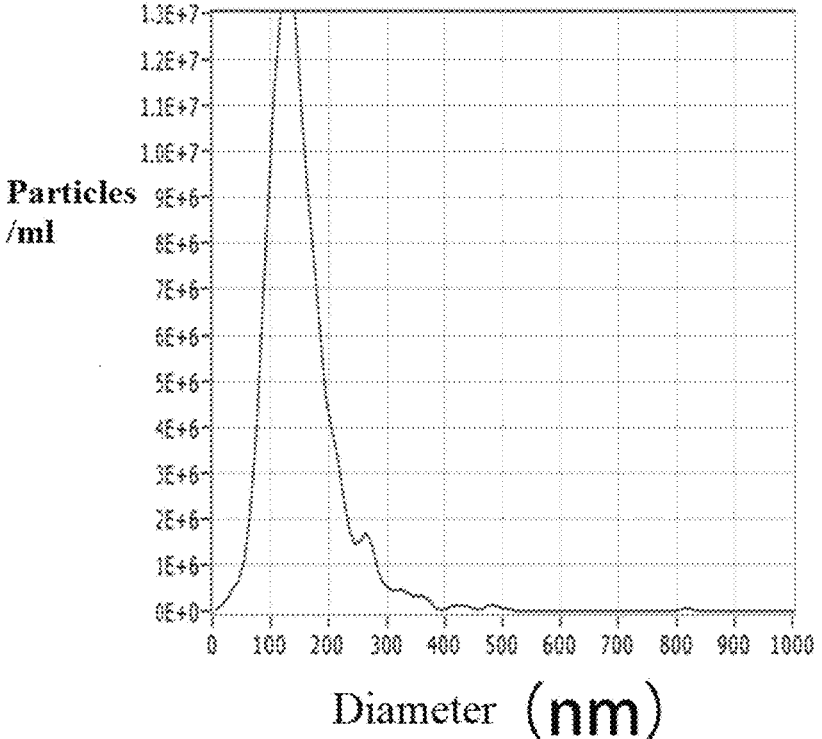
Figure 2:
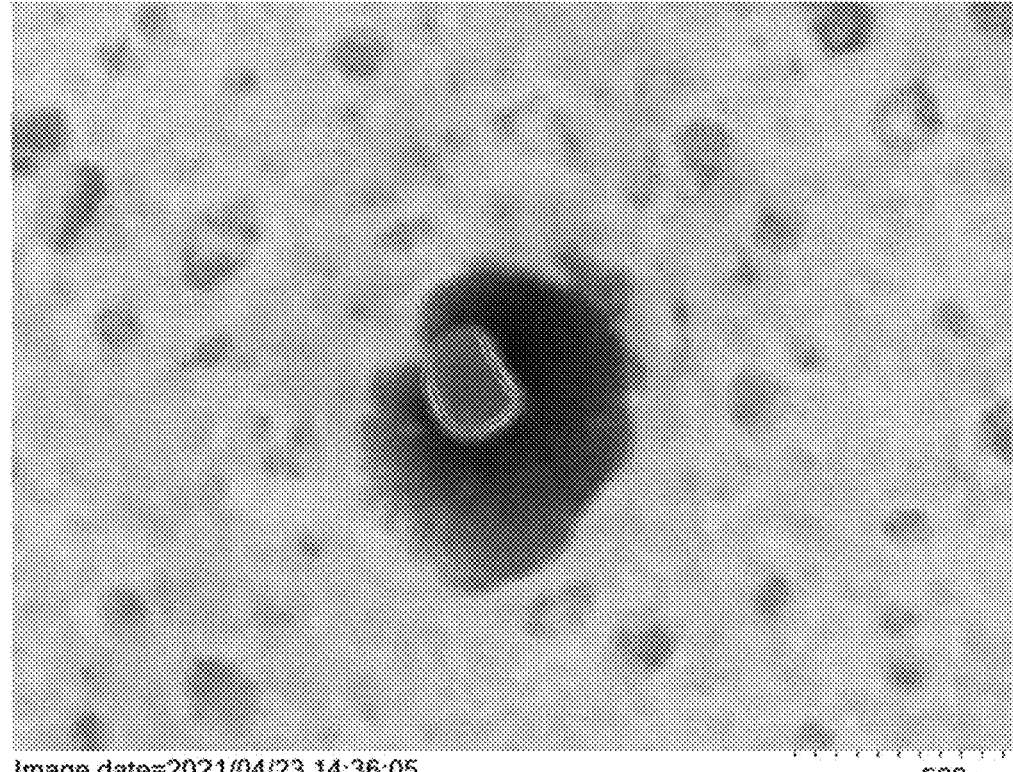
Figure 3:
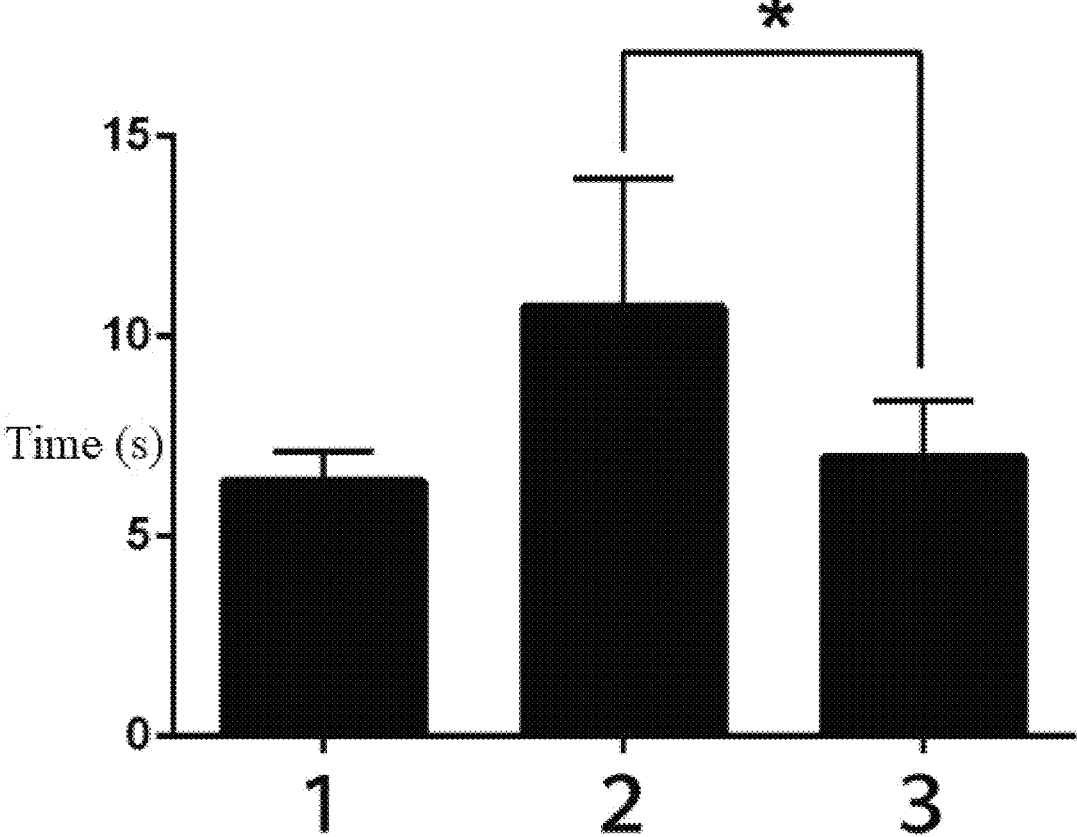
FIG. 3 shows that the BMSC-Exos improve a motor function of a model mouse with PD. 1: Control group; 2: MPTP group; 3: MPTP+exosome group. *$p < 0.05$; and a one-way ANOVA method is used for statistical analysis.
Figure 4:
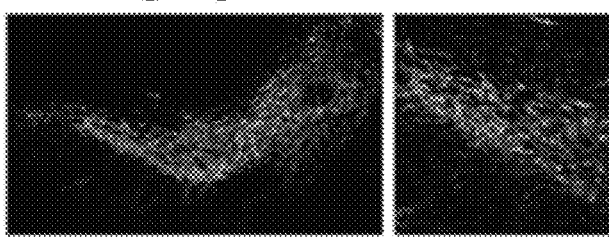
FIG. 4 shows that the BMSC-Exos improve the expression of tyrosine hydroxylase (TH) in substantia nigra of the model mouse with PD. The expression of TH (green) in substantia nigra of mouse is detected by an immunofluorescence staining method; and cell nucleuses are labeled with DAPI (4',6-diamidino-2-phenylindole; purple).
Figure 4:
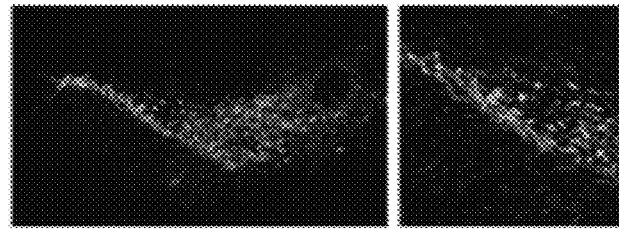
Figure 4:
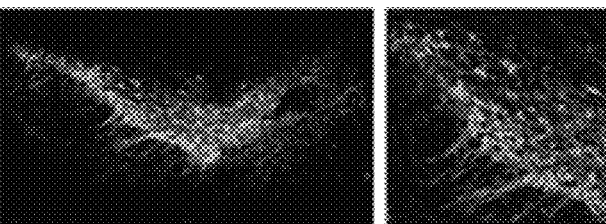
Figure 5:
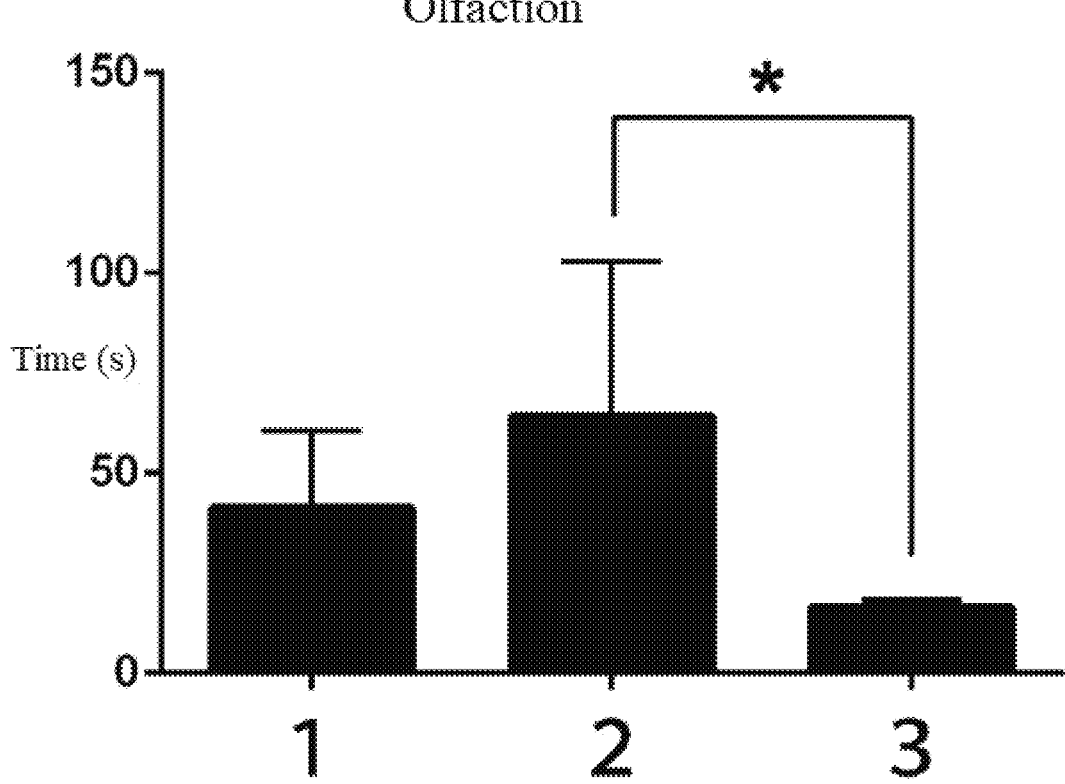
FIG. 5 shows that the BMSC-Exos improve an olfactory function of the model mouse with PD. 1: Control group; 2: MPTP group; 3: MPTP+exosome group. * $p < 0.05$; and the one-way ANOVA method is used for statistical analysis.
Figure 6:
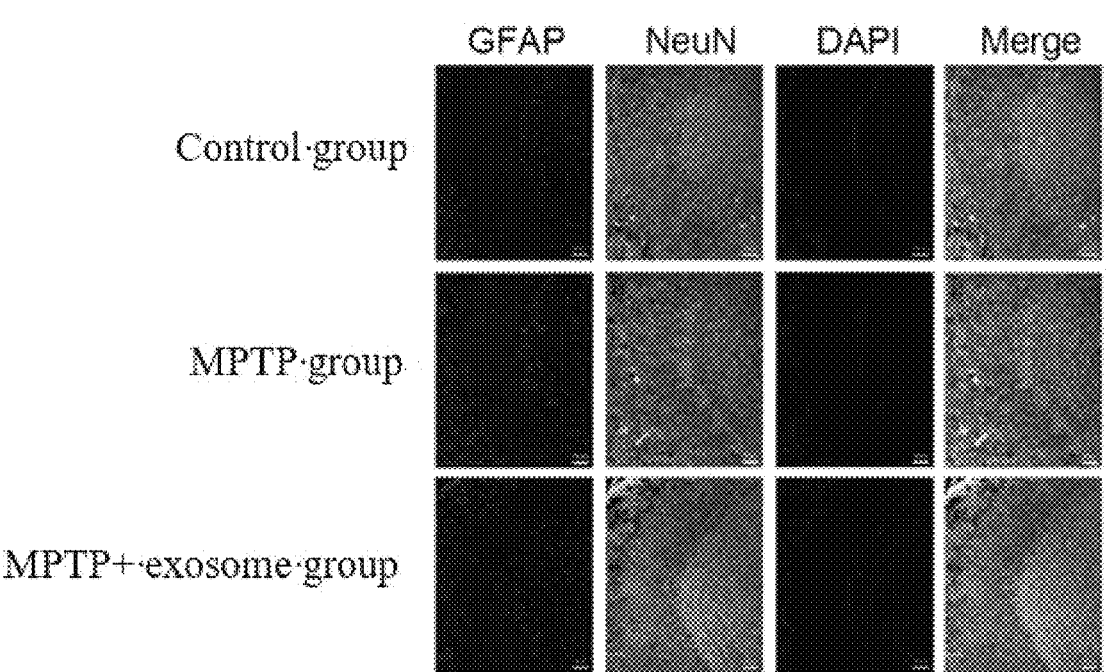
FIG. 6 shows that the BMSC-Exos reduce the expression of Glial Fibrillary Acidic Protein (GFAP) of olfactory bulbs of the model mouse with PD. The expression (red) of GFAP of an olfactory bulb region is detected by the immunofluorescence staining method; the neuron-specific nuclear protein (NeuN) is used for labeling neurons (green); and DAPI (4',6-diamidino-2-phenylindole; Purple) is used for labeling the cell nucleuses. Merge refers to a composite diagram.
Figure 7:
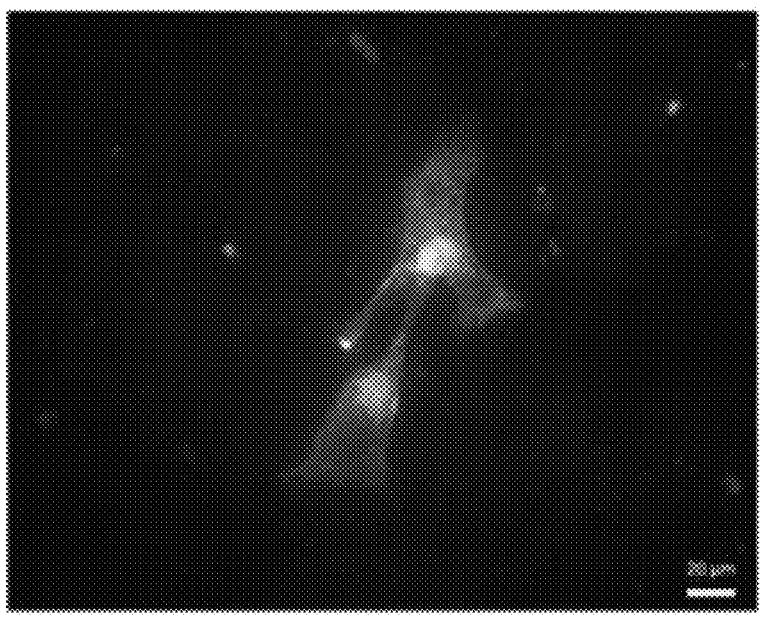
FIG. 7 shows internalization of the BMSC-Exos in olfactory neurons. The prepared exosomes are labeled with PKH-26 and then co-cultured with olfactory neurons of primary mouse. The immunofluorescence staining method is used for analyzing exocrine internalization. The labeled exosomes are red; and the olfactory neurons are labeled with TUJ1 (green).

As shown in FIG. 2, through the analysis of the prepared exosomes by the NTA, it is found that the average diameter of exosomes is 131.8 nm and the concentration is $7.4\times10^{10}$ particles/ml (FIG. 2B). Through the TEM, it is found that the exosomes are of a cup-shaped structure with double membranes (FIG. 2C). The results of pole test show that the treatment of exosomes can shorten the time required for the model mice with PD to complete pole climbing (FIG. 3). Through the detection for the expression of TH in substantia nigra, it is found that the treatment of exosomes can improve the expression of TH in substantia nigra of the model mice with PD (FIG. 4). The olfactory function experiment shows that the treatment of exosomes can shorten the time for the model mice with PD to find hidden food (FIG. 5). Through the immunofluorescence for the expression of GFAP of the olfactory bulb region, it is found that the treatment of exosomes can significantly reduce the expression of GFAP in the olfactory bulb region of the model mice with PD, which indicates that the activation of astrocytes in the olfactory bulb region is resisted (FIG. 6). The internalization experiment shows that the prepared exosomes can be taken up by the olfactory neurons (FIG. 7).

What is claimed is:

1. A method for preparing medicines for treating Parkinson's disease (PD) using human Bone Marrow Mesenchyml Stem Cell Exosomes (BMSC-Exos), comprising the following steps:
   stimulating the human BMSCs with a culture solution and generating the human BMSC-Exos; and
   extracting the human BMSC-Exos from the culture solution after passage, the culture solution of the human BMSCs is an Alpha Modified Eagle Medium (α-MEM) culture solution containing Fetal Bovine Serum (FBS) and Penicillin-Streptomycin Solution (PS);
   wherein, during culture the human BMSCs are digested with trypsin when the cell density reaches 80%, and are added with a complete medium of the α-MEM to terminate the digestion when it is observed that the cells become round and intercellular spaces become larger under a microscope; a supernatant is discarded after centrifugation, and the passage ratio is determined based on the number of cells; the cells are firstly passaged to form a P1 generation, the medium is completely replaced every 2 days, the cells are passaged to form a P2 generation after 4-6 days and then are digested again and passaged to form a P3 generation; and then, the P3 generation is used for extracting human BMSC-Exos;
   wherein a method for extracting the human BMSC-Exos comprises the following steps: collecting a supernatant of the human BMSCs, adding a buffer XBP with the same volume as the supernatant of the human BMSCs to be mixed uniformly, and filtering and collecting human BMSC-Exos with a membrane affinity spin column;
   wherein a method for collecting the supernatant of human BMSCs comprises the following steps: discarding the original culture medium when the P3 generation of human BMSCs grows to have a density of 80%; replacing with a serum-free α-MEM culture medium after washing twice with PBS, collecting the culture medium after continuing to culture for 48 h; and filtering to obtain supernatant after removing cell debris through centrifugation.

2. The method according to claim 1, wherein the medicines are used
   for improving a motor function in PD;
   for protecting dopaminergic neurons in PD;
   for improving an olfactory function in PD; or
   for reducing the activation of astrocytes in olfactory bulbs in PD.

3. The method according to claim 1, wherein the culture solution is an α-MEM culture solution containing 10% of FBS and 1% of PS.

4. The method according to claim 1, wherein the BMSCs are cultured at 37° C. and 5% of $CO_2$.

5. The method according to claim 1, wherein a bone marrow is inoculated in the complete medium preheated at 37° C.

6. The method according to claim 1, wherein the filtering method comprises filtering with a 0.22 μm filter membrane.

7. The method according to claim 1, wherein the centrifugation method comprises: centrifuging at force of 300 g at 4° C., and then centrifuging at force of 2000 g for 10 min.

\* \* \* \* \*